United States Patent
Kadota et al.

[11] Patent Number: 5,967,996
[45] Date of Patent: Oct. 19, 1999

[54] APPARATUS AND METHOD FOR AIDING TRANSMISSION

[75] Inventors: Toshihiko Kadota; Hiroyuki Ichiyoshi, both of Kawasaki; Hiroyuki Koizumi; Hideki Hayashi, both of Tokyo, all of Japan

[73] Assignee: Canon Kabushiki Kaisha, Tokyo, Japan

[21] Appl. No.: 08/820,353

[22] Filed: Mar. 12, 1997

Related U.S. Application Data

[63] Continuation of application No. 08/267,365, Jun. 29, 1994, abandoned.

[30] Foreign Application Priority Data

Jun. 30, 1993 [JP] Japan ................................. 5-160888

[51] Int. Cl.$^6$ .................................................. A61B 5/04
[52] U.S. Cl. ........................................ 600/544; 600/545
[58] Field of Search .................................. 600/544, 545, 600/546

[56] References Cited

U.S. PATENT DOCUMENTS

| | | | |
|---|---|---|---|
| 4,013,068 | 3/1977 | Settle et al. ..................... | 128/2.1 B |
| 4,140,997 | 2/1979 | Brady ................................. | 128/732 |
| 4,462,411 | 7/1984 | Rickards .............................. | 128/731 |
| 4,651,145 | 3/1987 | Sutter .................................. | 340/706 |
| 4,846,190 | 7/1989 | John ..................................... | 128/731 |
| 4,926,969 | 5/1990 | Wright ................................. | 128/731 |
| 4,987,903 | 1/1991 | Keppel et al. ...................... | 128/731 |
| 5,003,986 | 4/1991 | Finitzo et al. ...................... | 128/731 |
| 5,010,891 | 4/1991 | Chamoun ............................ | 128/731 |

FOREIGN PATENT DOCUMENTS

| | | |
|---|---|---|
| 0278989 | 8/1988 | European Pat. Off. . |
| 2128786 | 5/1984 | United Kingdom . |
| 2220089 | 12/1989 | United Kingdom . |

*Primary Examiner*—Robert L. Nasser
*Attorney, Agent, or Firm*—Fitzpatrick, Cella, Harper & Scinto

[57] ABSTRACT

An apparatus and a method for aiding the transmission of intent enables a severely physically-handicapped person, who has lost muscular energy due to amyotrophic lateral sclerosis (ALS), muscular dystrophy or the like, to transmit his/her intent through an electroencephalogram wave. A mechanical switch and an electroencephalogram wave switch are used in combination to allow the transmission of intent over the entire period of such a disease.

13 Claims, 14 Drawing Sheets

APPARATUS AND METHOD FOR AIDING TRANSMISSION

This application is a continuation, of application Ser. No. 08/267,365, filed Jun. 29, 1994, now abandoned.

BACKGROUND OF THE INVENTION

1. Field of the Invention

The present invention relates to an apparatus and a method for aiding the transmission of intent, which enable a severely physically-handicapped person, who has lost muscular energy due to amyotrophic lateral sclerosis (ALS), muscular dystrophy or the like, to transmit his/her intent through an electroencephalogram wave.

2. Related Background Art

The number of physically-handicapped persons, who lose motor functions while retaining their brain function, is expected to increase in the coming aged society. In the case of such diseases as ALS or muscular dystrophy, which are known as incurable diseases, patients' losing the means for transmitting their intent in medical care environments is leading to a significant increase in the medical care cost for medical treatment, medical attendance, and nursing. Further, there is strong demand for mutual transmission of intent between patients, who still retain human intelligence and senses, and people who attend on the patients over a long period.

A disease such as ALS and muscular dystrophy causes the muscular function of a human body to be lost slowly and no aiding apparatus is available for transmitting intent, which can be used over the entire period of the progressive disease of a patient.

A conventional apparatus, however, limits an input device to an external mechanical switch, whereas the mechanical switch is not suited to a patient suffering from the advancement of muscular anergic disease. The present invention combines a mechanical switch and an electroencephalogram wave switch to meet the demand for transmission of intent over the entire period of such a disease.

There is a human body feedback switch apparatus which employs the alpha wave among brain waves. The emergence of the alpha wave, however, varies greatly from one person to another, making it unsatisfactory as a control signal in the aspect of reliability accuracy; therefore, the switch apparatus is not used as a control switch for transmitting intent.

The conventional apparatus applies a general-purpose computer for non-handicapped persons and it is therefore disadvantageous to the physically-handicapped in that the operation is complicated and it is too large for them to handle easily. There is demand for a dedicated apparatus designed with an emphasis placed on ease of operation with a minimum of functions provided.

Figure 3:
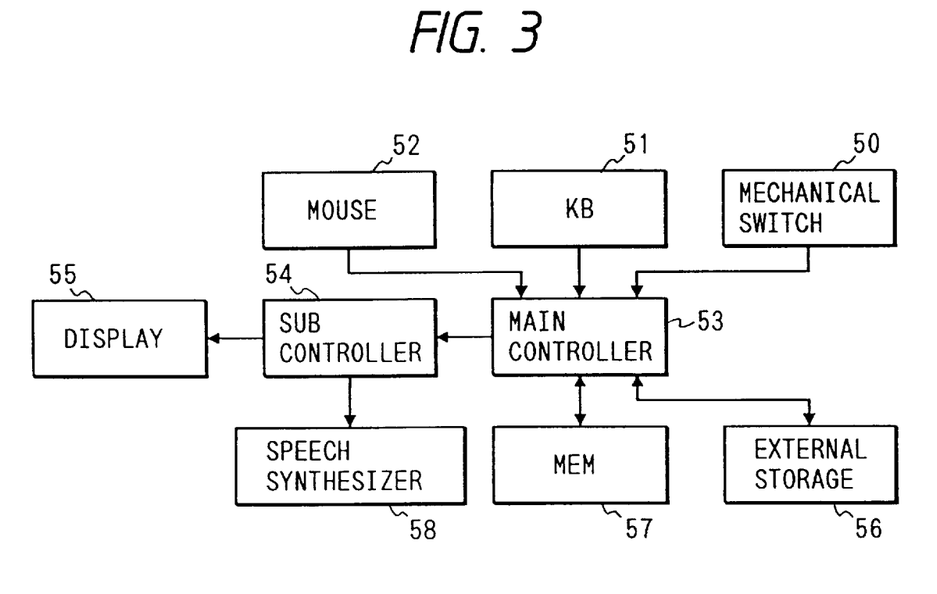
FIG. 3 is a configuration diagram of a conventional apparatus.

FIG. 3 is a block configuration diagram of a conversation aid apparatus, which applies a conventional general-purpose computer.

In the conversation aid apparatus, a main unit employs a general-purpose computer, which is equipped with a keyboard input device 51, a mouse input device 52, a main controller 53, which controls the constituents, a sub controller 54, which controls a display device 55 and a speech synthesizer 58, an external storage 56, and a memory 57, and it has an external input terminal of a control switch 50, which is operated by muscular strength.

As for conversational language, 960 daily conversational sentences, which are frequently used by physically-handicapped persons, are registered in the external storage 56 through a floppy disk. The registered sentences are displayed in sequence by switching the screen and a desired sentence is selected by using the mouse input device 52, the mechanical switch 50 or the like. Thus, the conventional apparatus is operated in a manner similar to that for a regular computer.

The conventional intent transmitting apparatus presents the following problems:

(1) The apparatus fails to enable a patient, who retains normal brain function, to use electroencephalogram wave other than muscular strength or to use it in combination.

(2) There is no interface available, which allows the apparatus to be used over the entire period of a progressive disease of a patient. The switch for confirming a selection is a mechanical switch, which is operated by muscular force and adapted to particular body movements. Therefore, the apparatus cannot be used when the patient loses his/her muscular strength, making it unsuitable for the physically-handicapped persons who are the target of the present invention.

(3) The use of the general-purpose computer with a keyboard, which is unnecessary for the user, adds weight to the apparatus. Further, the apparatus is equipped with accessories such as a voice synthesizer, adding to the size and complication, making the apparatus difficult to handle.

(4) The conventional software displays many different message sentences for daily conversation on a message display and allows selection of a desired message. For a severely physically-handicapped person, the more message selections they have, the more complicated and difficult operation they must execute. Hence, displaying a minimum of essential messages has become one of the requirements.

SUMMARY OF THE INVENTION

Accordingly, it is an object of the present invention to provide an apparatus and a method, which employs a compact, light-weight, and easy-to-handle apparatus and which is based on continued use of a message displaying method using an input control means, which are operated by muscular strength or brain waves according to the progression of a disease.

To fulfill the foregoing object, the present invention makes it possible to transmit intent by providing a brain wave switching circuit based on a brain wave detecting unit, which has a potential detecting circuit for extracting the beta wave component (an active current, which is generated in cerebral cells and nervous network in the cerebral cortex part when an intellectual activity of drawing a character or graphic image in the head in the course of human thinking or the like) of the brain waves, which is effectively used as a switch signal for determining a selection, and a switching device for input control operation through a mechanical switch device such as a micro-switch, which is operated by the muscular strength of a finger tip, toe, eyelid, etc., whereby to handle message characters, prepare words and sentences, and display on the screen of a character display under control, and by providing menu texts, a display for shewing the information of the text panel for preparing sentences, an alarm generator for calling up messages, an alarm controller, and a controller which controls the memory, the display, and the alarm controller.

The foregoing controller is characterized by a computing element built in and also by the brain wave switch based on the brain wave detecting unit, which configures a control means, that can be continuously used. Furthermore, the brain wave detecting unit for detecting active currents in the unit of a few μV of an effective brain wave component has an amplifier for each stage, an A/D converter, a digital band-pass filter, an integrator, and a controller for controlling the constituents, thereby producing fast, high-accuracy signals.

The foregoing storage device does not have any mechanical rotary mechanisms but it includes a volatile storage element or a non-volatile storage element. Further, the aforesaid display includes a non-thermal electronic element and it is located on the front surface of the main unit, no keyboard being provided. The character generation controller includes a non-volatile storage element and the characters, words, etc. are stored in advance. The function for transmitting voices is replaced by a method, wherein attention is drawn by the alarm generator, which generates an alarm sound, and the attention is led to a message on the display.

According to the present invention, the mechanical switch is provided with a controller based on a switch operating from brain waves in the system, which includes the aforesaid character generating unit for preparing message words and sentences and menu sentences (already registered message words and sentences) and graphic images, a recording unit comprising the storage element for registering them, and a display consisting of a non-thermal electronic element or the like such as liquid crystal, thus making it possible to specify a menu item (by confirming a selection through the switch) which corresponds to the intent of a user or to prepare a word or sentence by selecting (picking up by using the switch) characters from the character panel in a document preparing mode, thus allowing the intent information to be displayed on the display panel.

In the method for selecting the information shown on the display, an automatic interval search (variable parameter) function is used to blink in order an area of characters, words or sentences, which is displayed on the screen and which is available for selection; the selection can be confirmed by a single control signal given through the mechanical switch or the electroencephalogram wave switch, thus enabling the transmission of intent in terms of characters through easy operation.

Providing two types of input operating device enables a patient to use the switch unit, which is operated by muscular strength, in the early stage of a disease and to go through the training for operating the electroencephalogram wave switch as the patient loses the muscular strength according to the progression of the disease in the patient. The consistent operating procedure of the main unit of the apparatus permits minimized burden on the patient for learning how to operate it.

The computing element built in the control element and the use of a solid-state component for the recording unit have achieved faster processes.

The apparatus and method for aiding the transmission of intent according to the present invention provide the following effects:

1. Their use for transmitting patient's intent to the persons attending on or nursing the patient in medical care environments leads to higher efficiency in nursing.
2. Permits the transmission of intent of a patient, which is neglected in the medical science today, thus bringing out socially meaningful results. The apparatus employs a highly durable input control interface to prolong the service life of the apparatus.
3. The apparatus uses a dedicated system rather than a general-purpose computer; it features a minimum of required functions and easy operation, and it is ideally suited for clinical applications. Furthermore, it is compact and light-weight and it can be mounted on a post, thus saving installing space and exhibiting better portability.
4. The electroencephalogram wave processing and switch units can be applied as controllers having other functions to general-purpose applications.

DESCRIPTION OF THE PREFERRED EMBODIMENTS

The embodiment of the present invention will be explained in detail with connection to the attached drawings.

Figure 1:
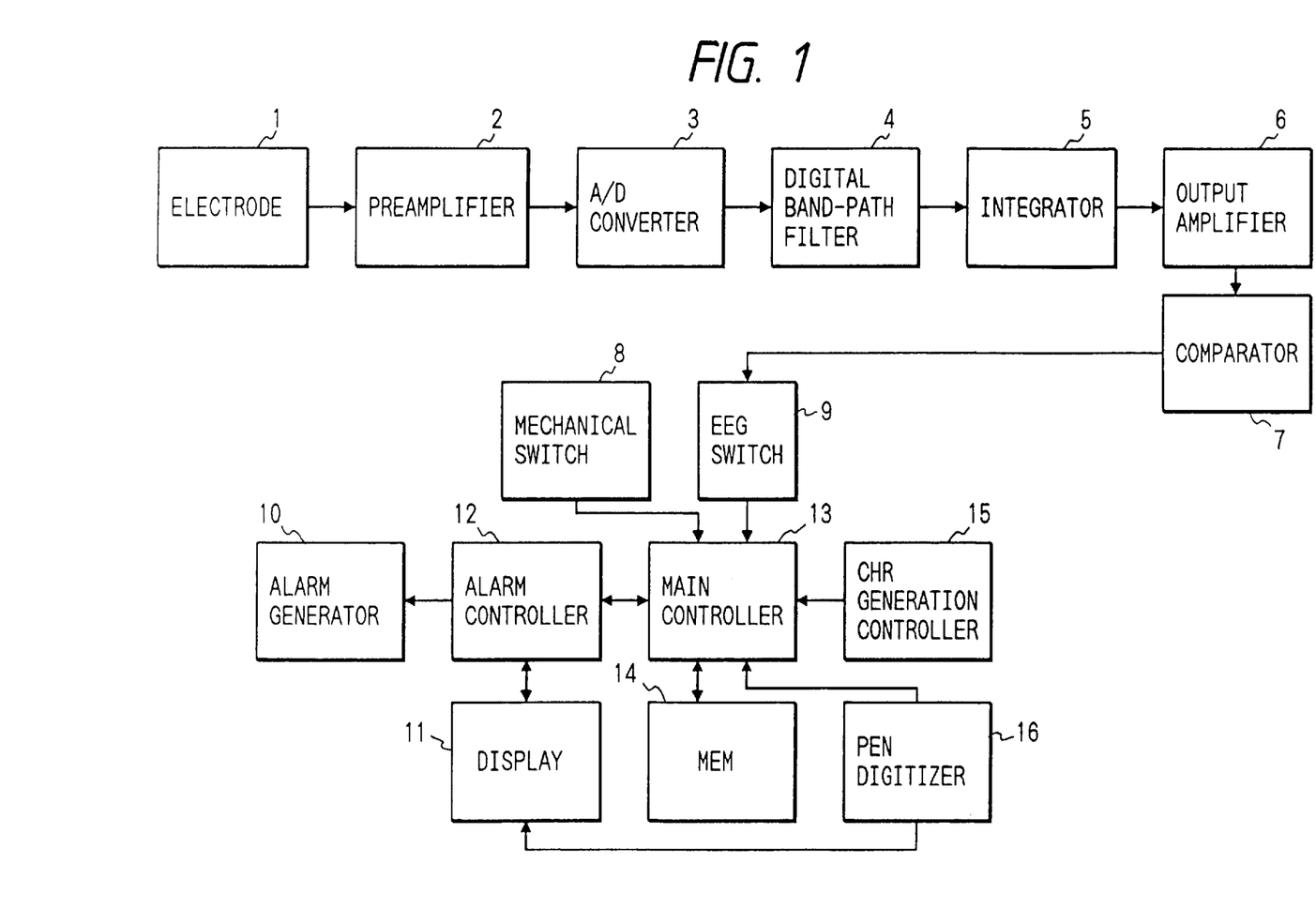
FIG. 1 is a block diagram showing the configuration of an apparatus, which embodies the present invention.

FIG. 1 is the block diagram illustrating the configuration of the apparatus for aiding the transmission of intent according to the present invention.

Figure 13A:
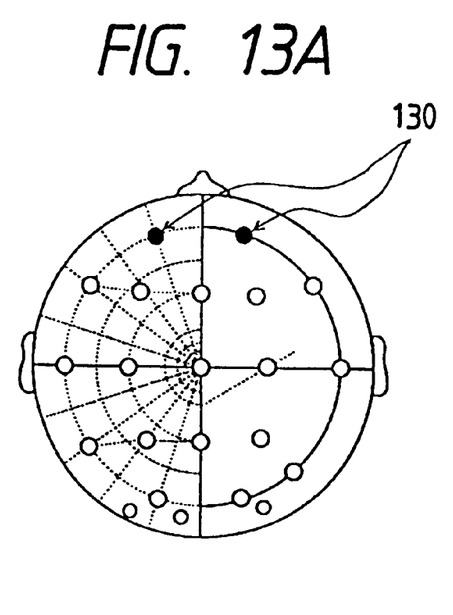
FIG. 13 is a diagram for illustrating the positions of electrodes through which brain waves enter.
Figure 13B:
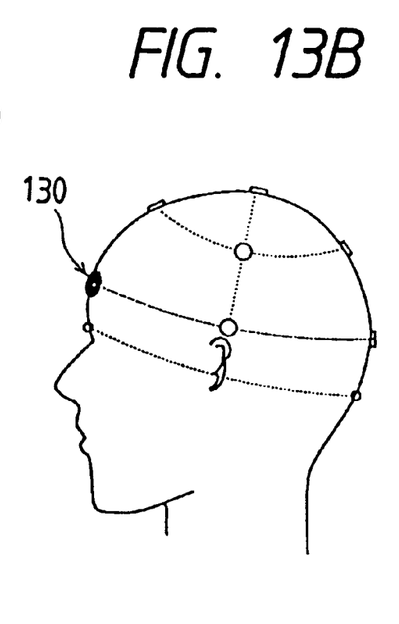

Numeral 1 denotes an electrode to be mounted on the forehead to detect currents generated in the head; it employs the bipolar lead-out method to efficiently catch a potential difference caused by the currents generated in the frontal lobe and the frontal area. The appropriate positions for mounting the electrodes are indicated by numeral 130 in FIG. 13.

Numeral 2 denotes an amplifier for amplifying a weak current in the level of a few microvolts caught at the electrodes 1; it is connected with 1 through an electrical lead wire.

Figure 14:
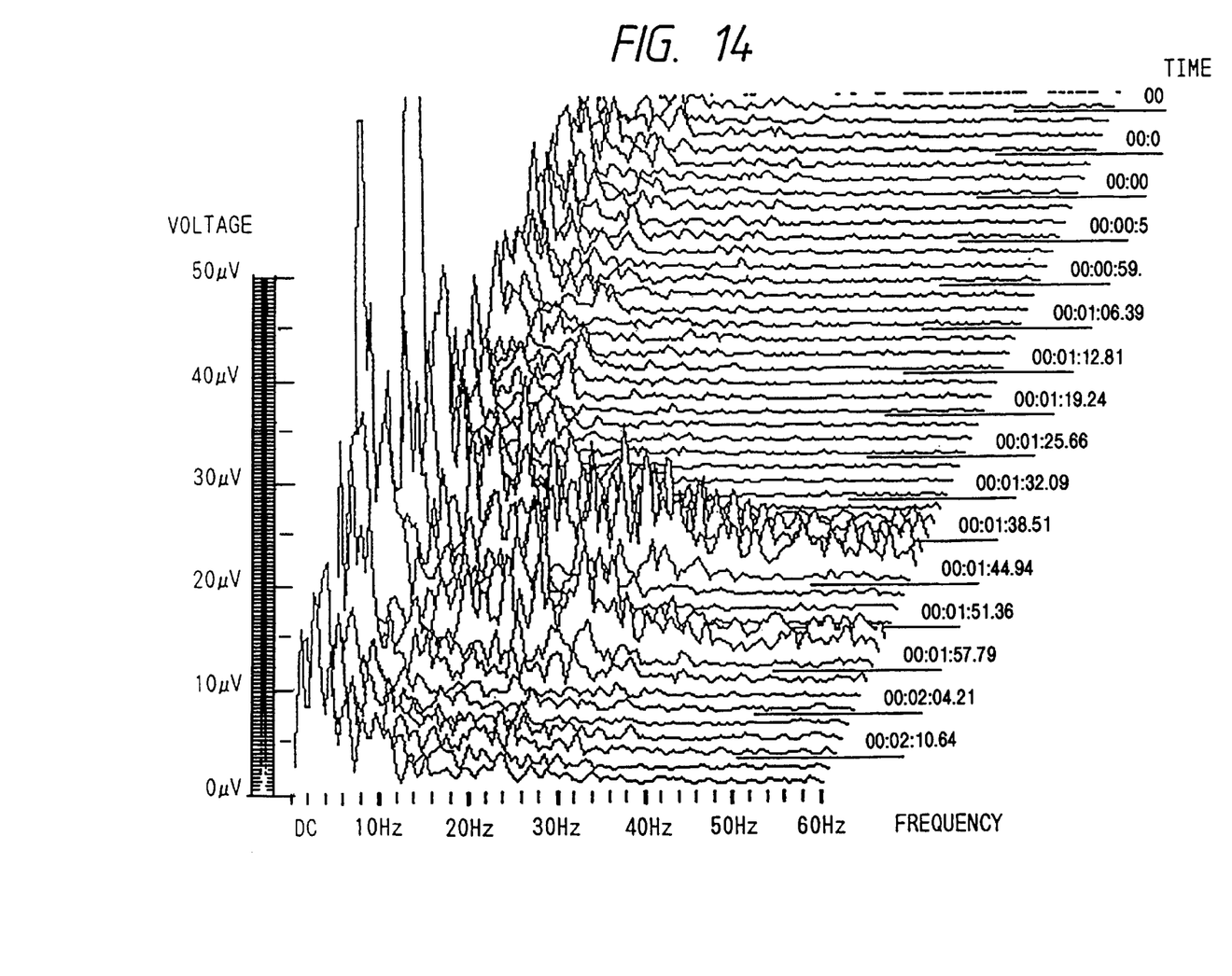
FIG. 14 is an example of a diagram obtained by subjecting brain waves to A/D conversion.

Numeral 3 denotes a converter, which converts an analog signal to a digital signal for improving the accuracy of extracting a frequency peak component. A waveform after conversion is illustrated in FIG. 14. The axis of abscissa indicates frequency, the axis of ordinate indicates the magnitude of current, and the depth indicates time.

Numeral 4 denotes a frequency band-pass filter for the frequency component band to be used, mainly the beta-wave high frequency band of 20 to 40 Hz. By passing brain waves through this filter, the data of the frequency band necessary for being used as the brain wave switch are extracted from the brain waves measured through the electrode 1.

Numeral 5 denotes a circuit for integrating peak currents in the brain wave beta-wave frequency, which can be used for the brain wave switch. Numeral 6 denotes an output amplifier, which amplifies a signal of 5 into a stable signal. Numeral 7 indicates a comparator for determining the level of an output signal in relation to a reference signal when turning the brain wave switch ON; it outputs to an electroencephalogram switch 9 that the level of an output signal has exceeded the level of the reference signal. The comparator serves also as a level adjustor.

When an output of the comparator 7 indicates that the brain wave in the beta-wave frequency band has reached a satisfactory level and the brain wave switch should be turned ON, the electroencephalogram switch 9 applies a control signal for turning the switch ON to the controller of the main unit message display.

Numeral 8 is an input unit consisting of a mechanical switch such as a microswitch operated by muscular strength of a part of a human body; it is connected to the main controller via a connection terminal.

Figure 4:
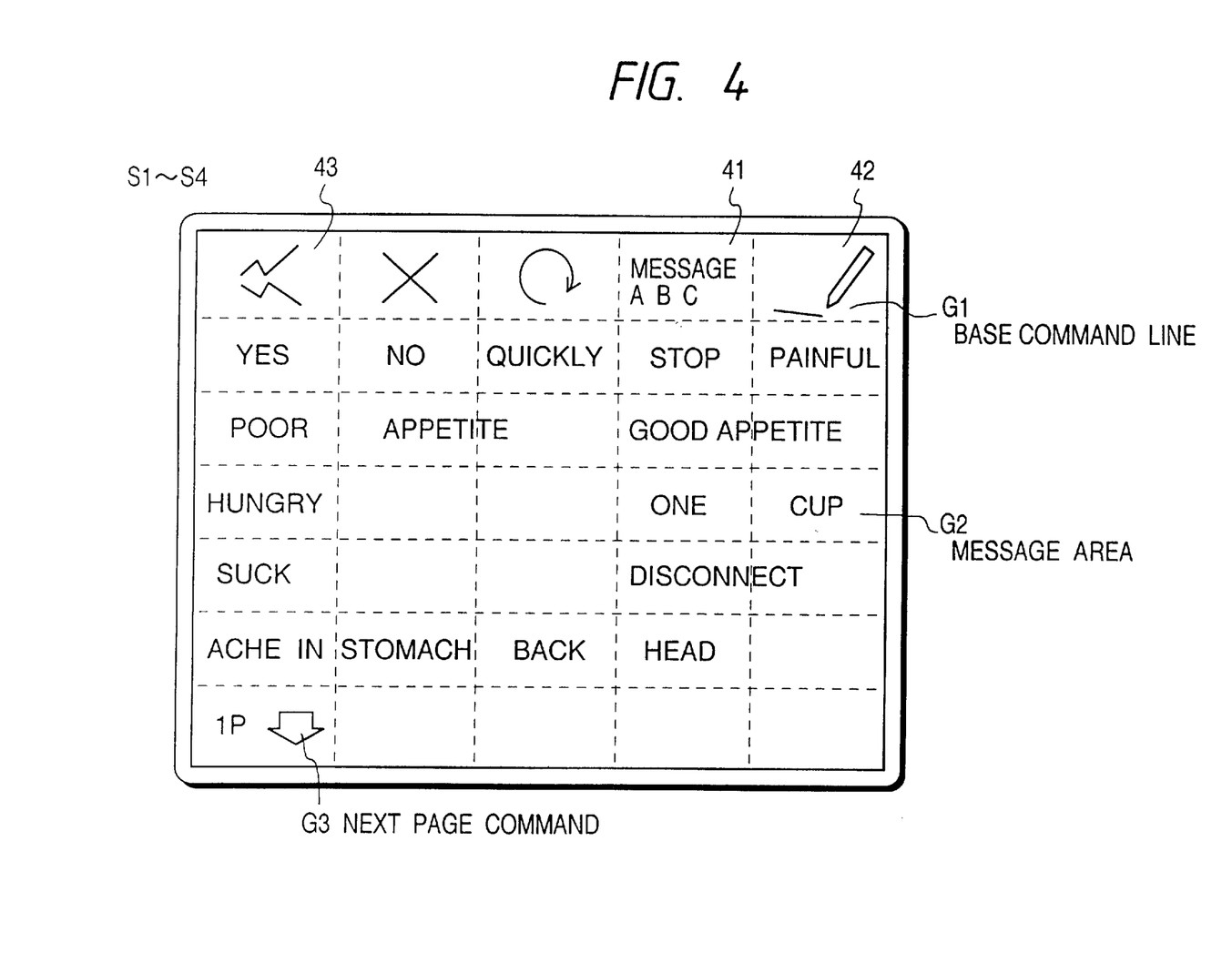
FIG. 4 illustrates the display examples for S1 through S4.

Numeral 11 denotes a display of the main unit message processor, which displays a message for transmitting intent on the screen. Numeral 16 denotes a pen digitizer for entering drawn information such as characters in the form of coordinate data. Numeral 10 is an alarm generator, which is actuated in response to an input instructing the generation of an alarm when confirmation is made or when a cell 43 in FIG. 4 is selected. Numeral 12 is an alarm controller, which controls 10.

Numeral 15 is a character generation controller having a font ROM, which is used in a menu selection mode and a word processing mode; it generates character data to display desired characters on the display 11 and it has a simple character recognizing function to recognize a character drawn on the digitizer 16 when a cell 42 of FIG. 4 is selected to instruct the digitizer input mode.

Numeral 14 indicates a memory for storing sentences, words and graphic images created by using 15 and 16 and also a control program for the processing procedure shown in the flowchart to be discussed later; it includes a ROM (read-only memory) and a RAM (random-access memory).

Numeral 13 denotes a controller (CPU), which consists of a microcomputer having a computing element, which features low power consumption and fast computation; it controls the units described above in accordance with the control program stored in the memory 14. More specifically, the controller has the following control functions:

(1) Controls the arithmetic operation of the integrator, comparator, etc. of the electroencephalogram wave processor.
(2) Controls the lighting of the XY search of the display 11 and a selected item of 12 and the blinking for confirmation.
(3) Sets the parameter for the interval search in (2) above.
(4) Controls the switches 8 and 9 and also controls the confirmation signals of the display and the return to an initial mode.
(5) Controls 15, 16, and the character generation controller 15 related to 12.

Figure 2:
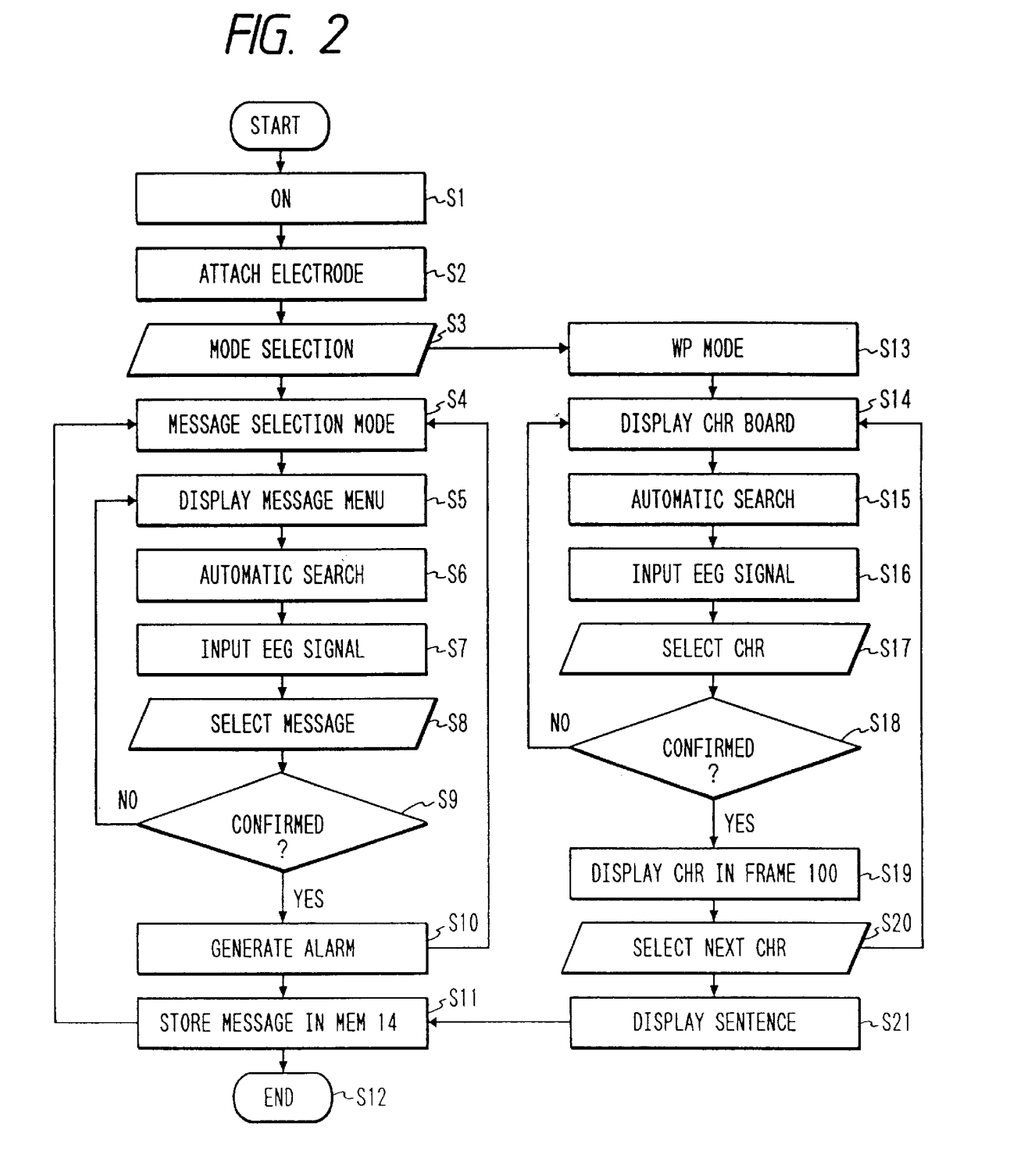
FIG. 2 is a flowchart showing the processing procedure in the embodiment.
Figure 9:
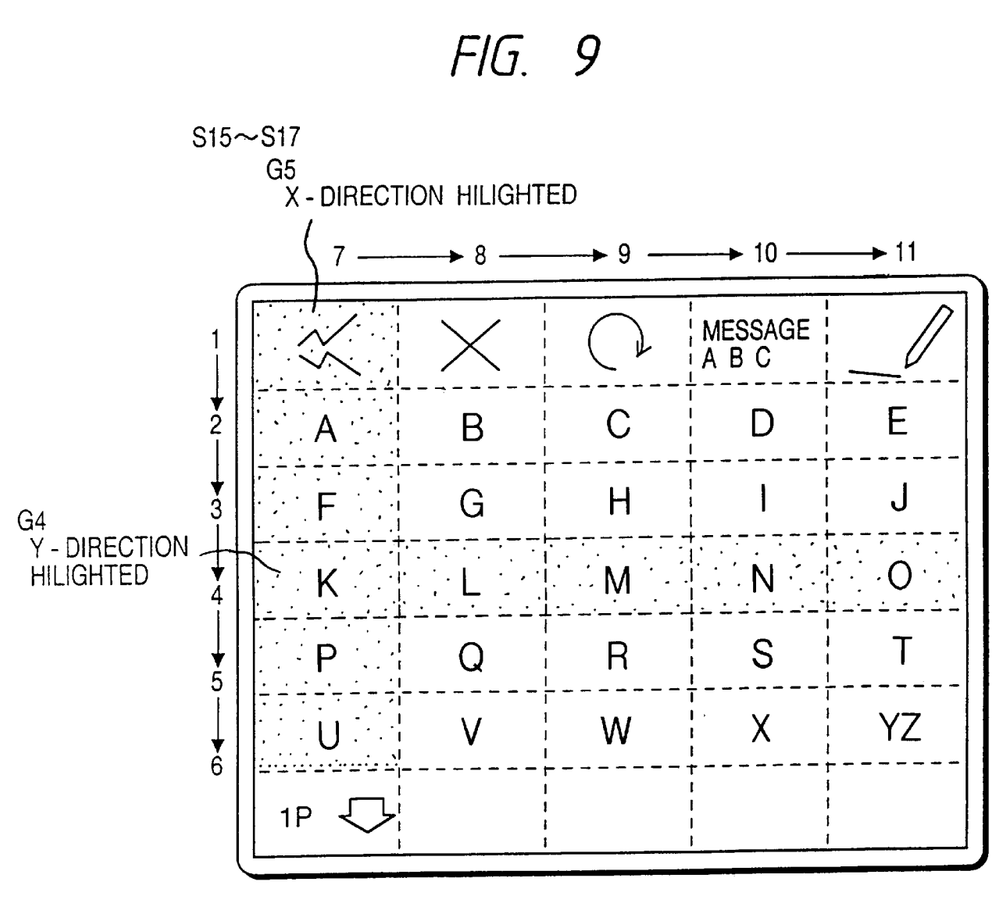
FIG. 9 illustrates the display examples for S15 through S17.

The flow of the processing in the apparatus for aiding the transmission of intent in FIG. 9 will now be described with reference to the flowchart shown in FIG. 2.

First, the operation is started when a main unit power switch is turned ON in a step S1. Then in S2, the electrode attached to a head band or the like is mounted on the forehead.

In S3, the display 11 shows an initial screen, which has an area of a basic command line G1 to allow the selection of a mode as shown in FIG. 4. A cell 41 shows that a message selection mode, which is the main mode, has been selected ("MESSAGE" is highlighted). At this time, if the cell 41 is not specified, then the system determines that an instruction for changing the mode has been given and it selects the word processing mode, which is different from the mode selected when the cell 41 was specified, and it reports to an operator that the currently selected mode is the word processing mode by highlighting "ABC."

In S3, if the message selection mode is selected by a switch input signal, then the system starts the processing for the message selection mode (S4).

In S5, a list of message menus already registered is read out from the memory 14 and shown on the display 11 as illustrated in FIG. 4.

Figure 5:
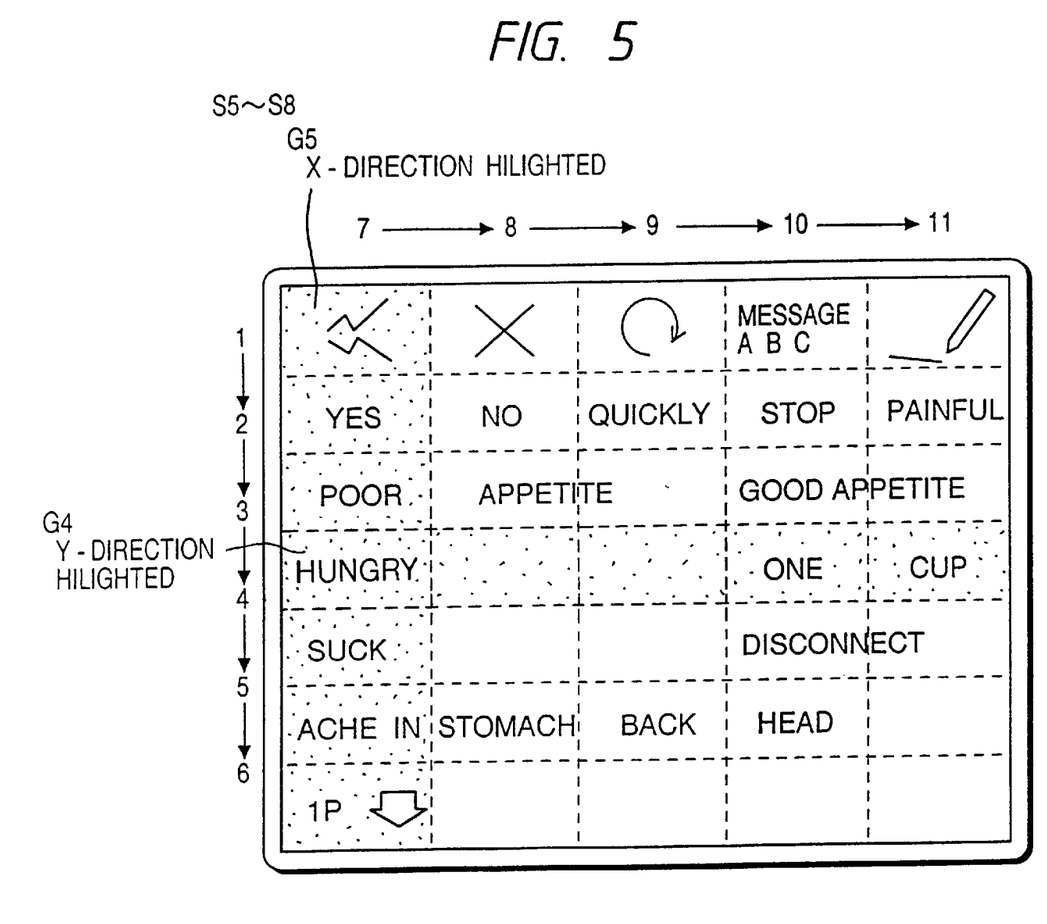
FIG. 5 illustrates the display examples for S5 through S8.

In S6, as shown in FIG. 5, the system starts automatic search at a given time intervals in direction X and direction Y of the square cells of the message list. For instance, the system first advances 1 to 5 steps in the direction of Y axis, then in the direction of X axis for 6 to 11 steps in order at intervals of 1 to 10 seconds (the parameter is set), thus repeating the automatic interval search. A step, wherein a confirmation signal is entered on Y axis, is kept ON, skipping the rest, and the system starts search turning ON in the direction of axis X from 7 of G5. The parameter for the time interval of the automatic search is set according to a method to be discussed later. A string of items to be approved is illuminated brighter by one level, all strings being lighted in order at regular intervals.

The user takes voluntary actions such as reading or drawing at a selected area, thus generating the active brain current in the frontal area. The generated active brain current is detected as a potential in the scalp through the electrode 1, and the electroencephalogram wave component is processed; if the electroencephalogram wave switch 9 detects the information, which indicates that the electroencephalogram wave switch should be turned ON, then an ON switch signal is output to the controller 13 (S7).

Figure 6:
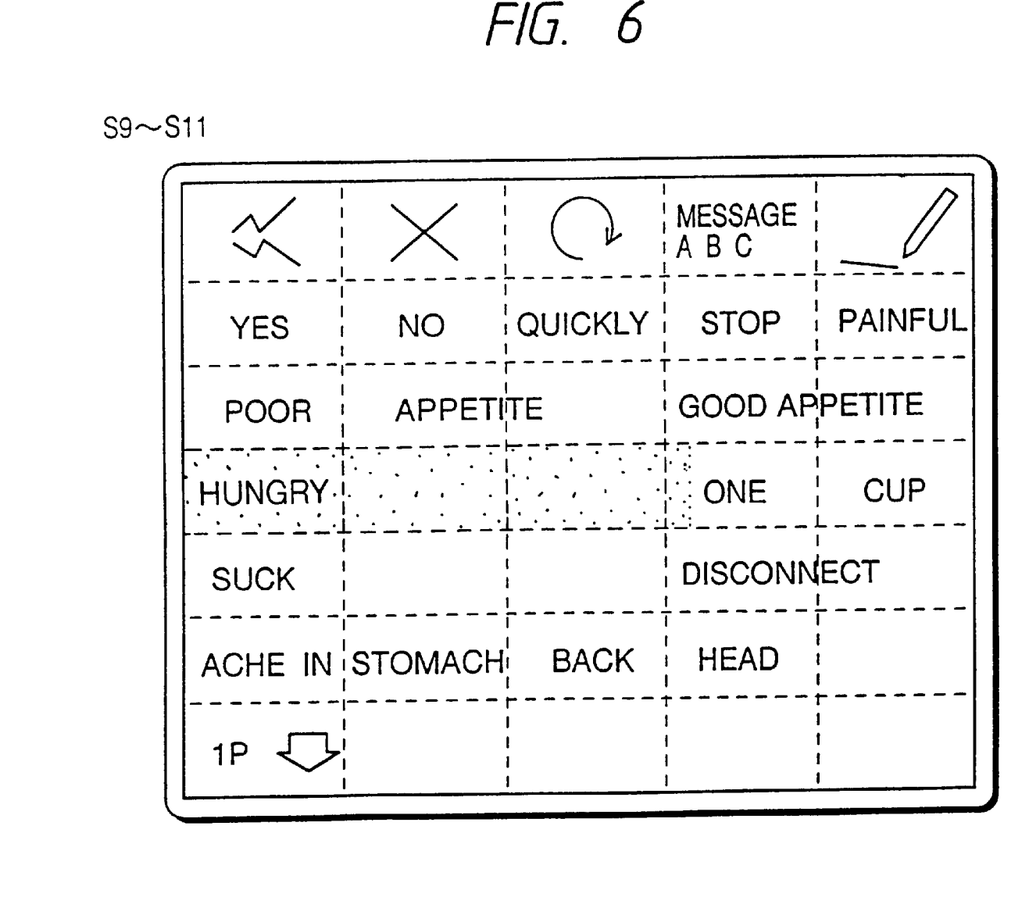
FIG. 6 illustrates the display examples for S9 through S11.

When a signal is issued by the switch 9, a cell, which is ON at that moment, is selected as the message (S8). This completes the confirming operation, and the system shows the selected cell by blinking it as shown in FIG. 6 (S9).

Figure 7:
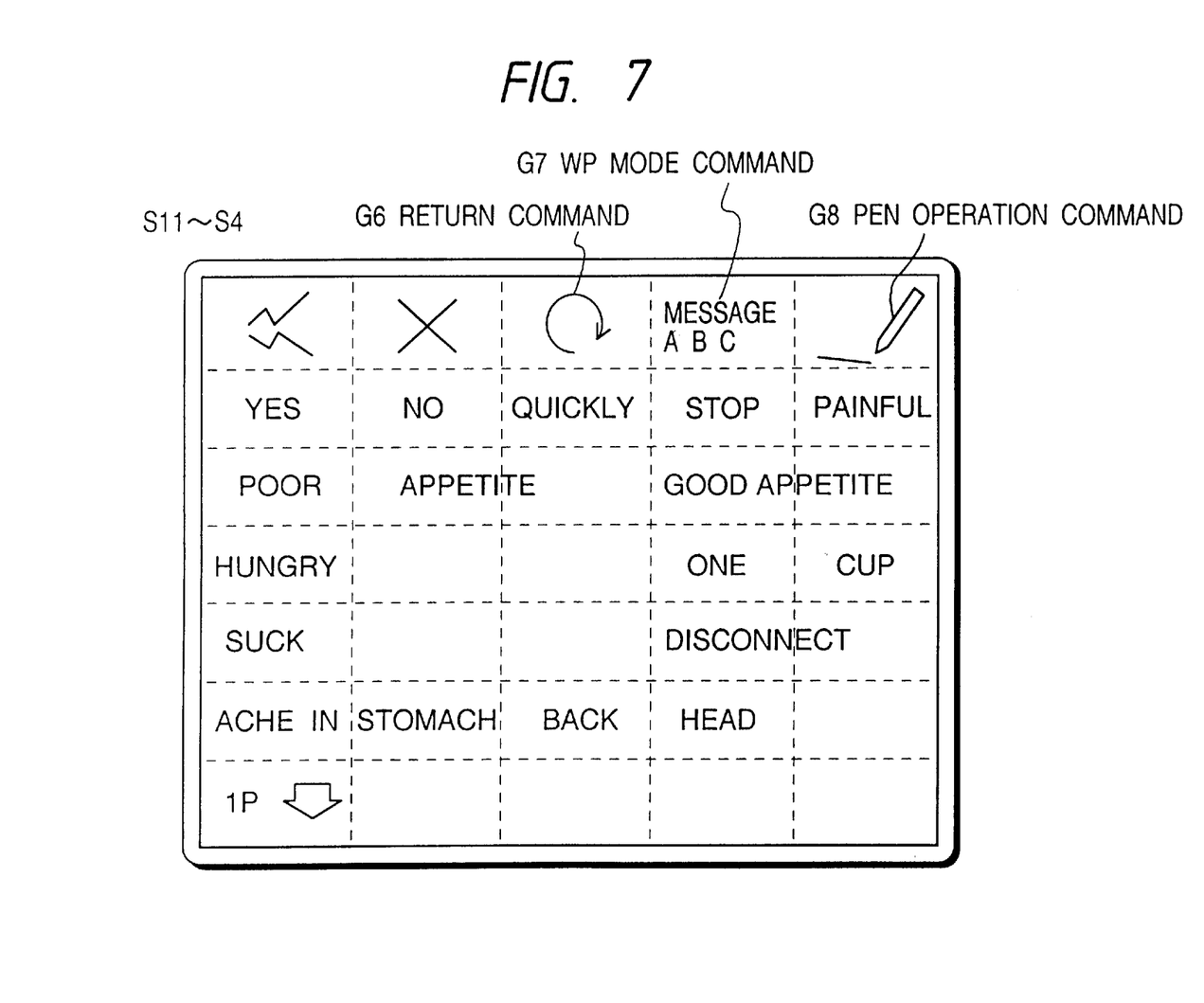
FIG. 7 illustrates the display examples for S11 through S4.

In S10, an alarm sound for notifying the presence of a message for transmitting intent is given by the alarm generator 10. The messages confirmed in S9 are stored in the memory 14 in the order in which they were confirmed (S11), and the system goes back to the initial screen display of the message selection mode as shown in FIG. 7 then repeats the processing, starting with S4 by selecting a return command G6 and confirming the selection. After the processing of S11, if no input is given for a certain time or if a cell of "END" (not shown) is selected, then the system terminates the processing (S12).

Direct drawing in a registration frame may be performed through the pen digitizer 16. Further, a pointing device may be used to specify a position.

Figure 8:
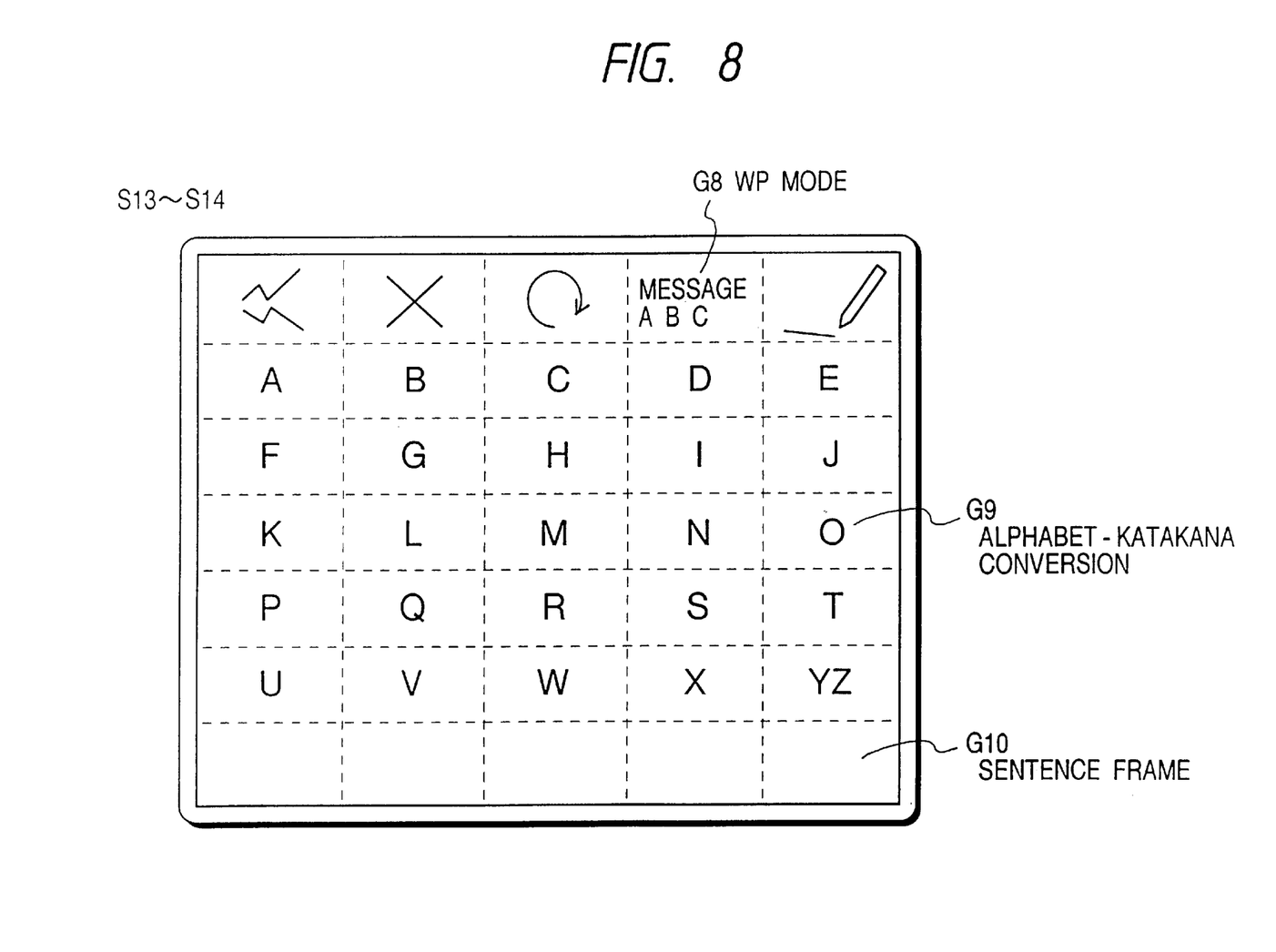
FIG. 8 illustrates the display examples for S13 and S14.

In S3, if the cell 41 is selected to switch to the word processing mode by a word processing command G7, then the system starts the word processing mode in S13. The display information for the word processing mode is read out from the memory 14 and a character board showing characters, including alphabets and katakana displayed, in the squares appears as shown in FIG. 8 (S14).

Figure 10:
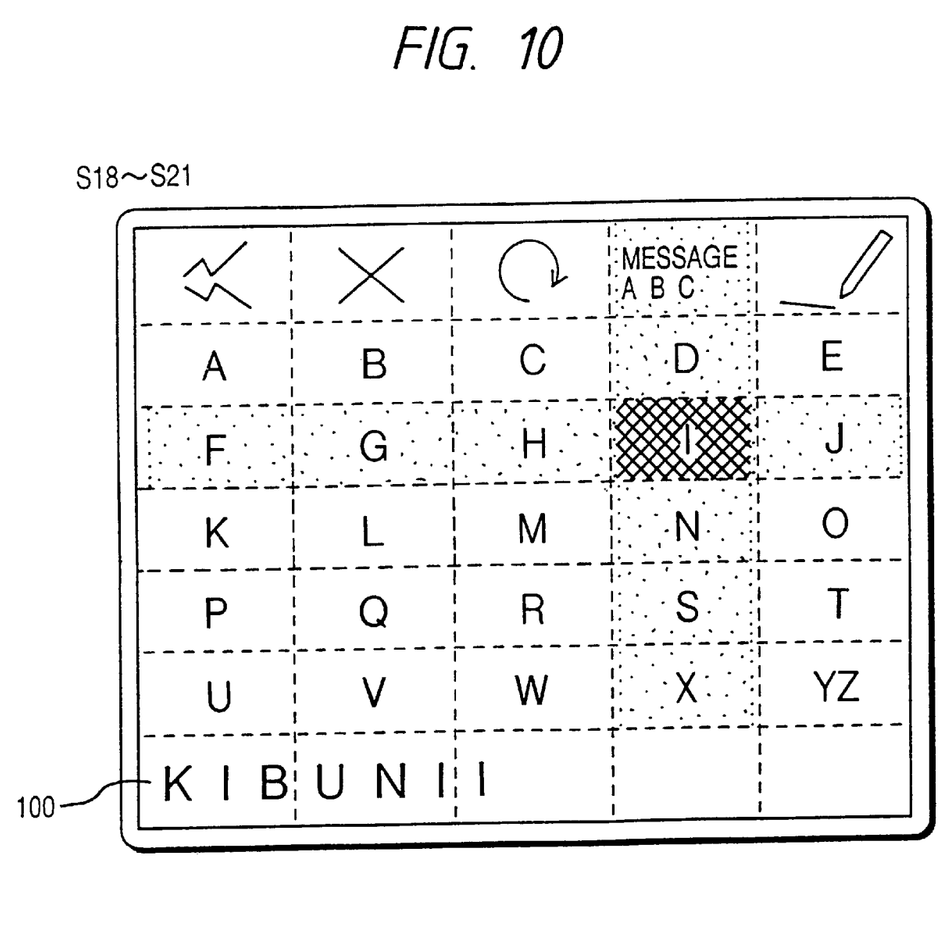
FIG. 10 illustrates the display examples for S18 through S21.

In S15, the automatic search of character strings is started in the X and Y directions as in S6. Then in S16, the brain waves generated by taking actions such as drawing in the head or reading are detected as in S7; in S17, characters are selected as in S8, and in S18, confirmation is performed as in S9. The characters thus selected are arranged and displayed in order in a sentence frame 100 as shown in FIG. 10 (S19).

Figure 11:
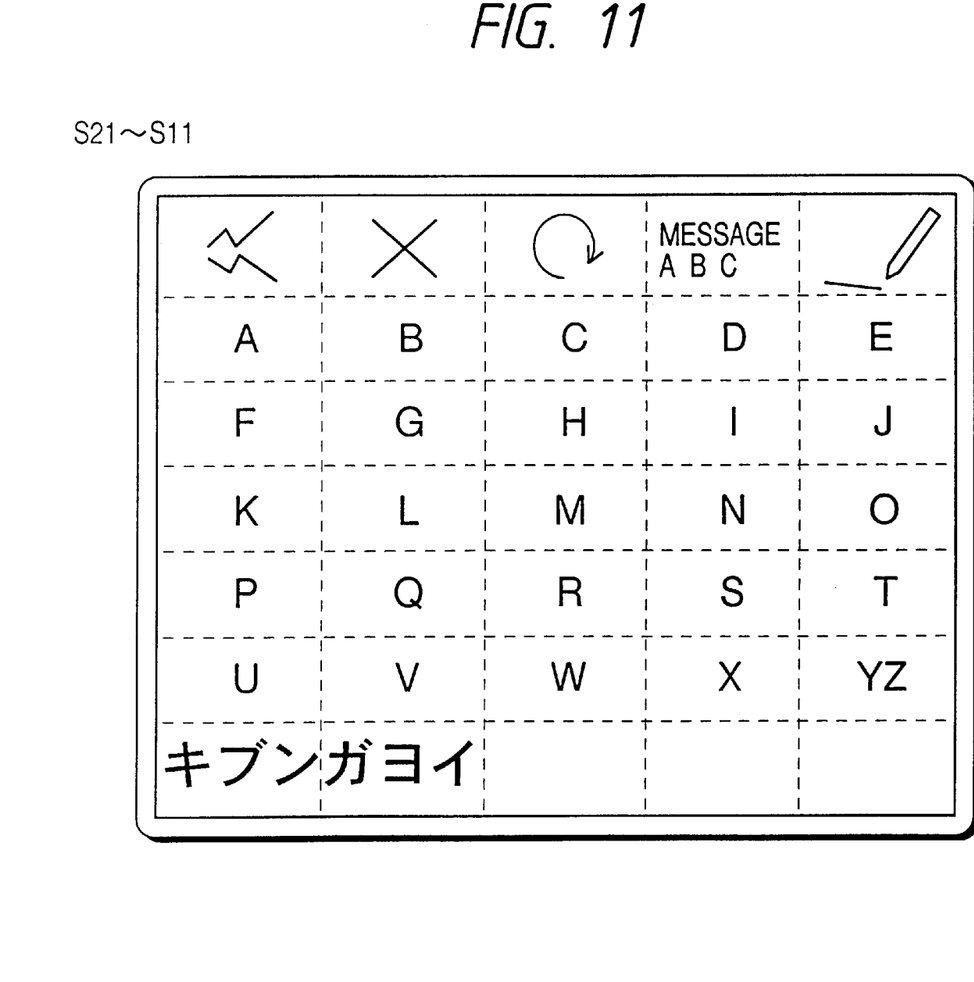
FIG. 11 illustrates the display examples for S21 through S11.
Figure 12:
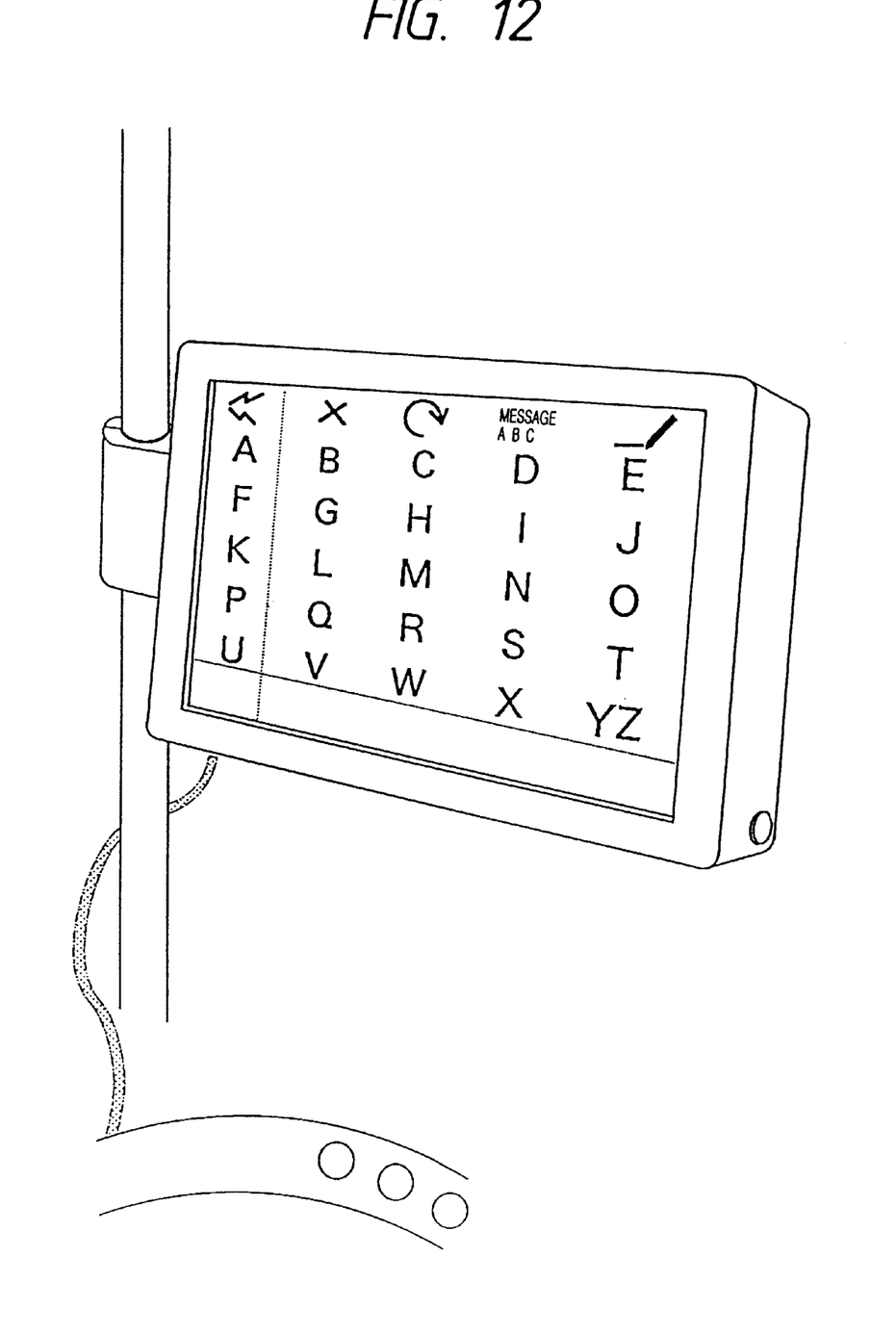
FIG. 12 is an external view.

A message sentence or word is created by repeating the steps from S14 to S20. The system proceeds to S21 if no input is given for a certain time in S20. The sentence or word created in S21 is stored in the memory 14. The characters selected in S17 may be displayed in alphabets ("KIBUNII" (feel better)) in the sentence frame 100 as shown in FIG. 10 or they may alternatively be converted to katakana and displayed as shown in FIG. 11.

The apparatus has the mechanical switch 8, so that the operator of the apparatus operates the mechanical switch as long as the operator retains muscular strength while at the same time taking voluntary actions such as reading and writing characters to turn the electroencephalogram wave switch ON. The difference between the turning ON timing of the mechanical switch and that of the electroencephalogram wave switch is detected, and the time interval of the automatic search performed in S6 and S15 of the flowchart shown in FIG. 2 is set in accordance with the difference. Storing the parameter in the memory 14 permits efficient automatic search display, which matches the characteristics of the operator and the characteristics of the apparatus.

What is claimed is:

1. An apparatus for aiding transmission of intent, comprising:

displaying means for displaying a plurality of character patterns;

determining means for determining whether a signal level based on currents of a beta-wave frequency band of a brain wave exceeds a predetermined level;

control means for controlling said displaying means such that a character pattern available for selection is displayed distinguishably from the other character patterns;

changing means for sequentially changing the character pattern available for selection from one character pattern to another on said displaying means; and selecting means, responsive to a determination by said determining means that the signal level based on currents of the beta-wave frequency band of the brain wave exceeds the predetermined level, for selecting the character pattern distinguishably displayed by said displaying means.

2. An apparatus according to claim 1, wherein the beta brain wave has a frequency within the range of 20 to 40 Hz.

3. An apparatus according to claim 1, further comprising a mechanical switch for selecting the distinguished character pattern.

4. An apparatus according to claim 3, further comprising determining means which determines a time interrelationship between an input given by said mechanical switch and the detection of the brain wave by said detecting means and registers the time.

5. An apparatus according to claim 1, further comprising storing means for storing a message, said controlling means controlling said displaying means so that a message stored in said storing means may be displayed on said displaying means.

6. An apparatus according to claim 4, wherein the selection of a character pattern by said selecting means is controlled in accordance with the time interrelationship which is determined and registered by said determining means.

7. A method for aiding transmission of intent, comprising:

displaying a plurality of character patterns on a display device;

determining whether a signal level based on currents of a beta-wave frequency band of a brain wave exceeds a predetermined level;

controlling the display device such that a character pattern available for selection is displayed distinguishably from the other character patterns;

sequentially changing the character pattern available for selection from one character pattern to another on the display device; and selecting, in response to a determination that the signal level based on currents of the beta-wave frequency band of the brain wave exceeds the predetermined level, the character pattern distinguishably displayed on the display device.

8. A method according to claim 7, wherein the detecting step is applied to the brain wave having a frequency within a range of 20 to 40 Hz.

9. A method according to claim 7, further comprising the step of providing a mechanical switch for selecting the distinguished character pattern.

10. A method according to claim 9, further comprising the step of determining a time interrelationship between an input given by the mechanical switch and the detection of the brain wave and registering the time.

11. A method according to claim 7, further comprising the step of registering the display character pattern as a message.

12. A method according to claim 10, further comprising the step of controlling the selection of the character pattern in accordance with the registered time interrelationship.

13. A computer-readable medium recording computer program for aiding transmission of intent, the computer program comprising:

a displaying module for displaying a plurality of character patterns on a display device;

a determining module for determining whether a signal level based on currents of a beta-wave frequency band of a brain wave exceeds a predetermined level;

a controlling module for controlling the display device such that a character pattern available for selection is displayed distinguishably from the other character patterns;

a changing module for sequentially changing the character pattern available for selection from one character pattern to another on the display device; and a selecting module for selecting, in response to a determination that the signal level based on currents of the beta-wave frequency band of the brain wave exceeds the predetermined level, the character pattern distinguishably displayed on the display device.

* * * * *

UNITED STATES PATENT AND TRADEMARK OFFICE
CERTIFICATE OF CORRECTION

PATENT NO. : 5,967,996
DATED : October 19, 1999
INVENTOR(S) : Toshihiko Kadota, et al.

It is certified that error appears in the above-identified patent and that said Letters Patent is hereby corrected as shown below:

Column 2:
Line 61, "shewing" should read -- showing --.

Column 4:
Line 34, "13" should read -- 13A and 13B -- and "is a diapram" should read -- are diagrams --.
Line 53, "FIG.13." should read -- FIGS. 13A and 13B. --.

Signed and Sealed this

Eighteenth Day of September, 2001

*Attest:*

NICHOLAS P. GODICI
*Attesting Officer*    Acting Director of the United States Patent and Trademark Office